US006689788B1

(12) United States Patent
Bergeron, Jr.

(10) Patent No.: US 6,689,788 B1
(45) Date of Patent: *Feb. 10, 2004

(54) METHOD AND COMPOSITION FOR TREATMENT OF INFLAMMATORY BOWEL DISEASE

(75) Inventor: Raymond J. Bergeron, Jr., Gainesville, FL (US)

(73) Assignee: University of Florida, Gainesville, FL (US)

( * ) Notice: Subject to any disclaimer, the term of this patent is extended or adjusted under 35 U.S.C. 154(b) by 150 days.

This patent is subject to a terminal disclaimer.

(21) Appl. No.: 09/645,507

(22) Filed: Aug. 25, 2000

(51) Int. Cl.[7] .......................................... A61K 31/435
(52) U.S. Cl. ..................... 514/277; 514/2; 514/279; 514/300; 514/359; 514/365; 514/367; 514/408; 514/423; 542/152; 542/200; 542/201; 542/400; 542/452; 542/469; 562/623
(58) Field of Search ................ 514/2, 277, 279, 514/300, 359, 365, 367, 408, 423; 548/152, 200, 201, 400, 452, 469; 562/623

(56) References Cited

U.S. PATENT DOCUMENTS

| | | | |
|---|---|---|---|
| 5,110,795 A | 5/1992 | Hahn | 514/17 |
| 5,112,856 A | 5/1992 | Gaginella et al. | 514/456 |
| 5,216,002 A | 6/1993 | Gidda et al. | 514/369 |
| 5,238,931 A | 8/1993 | Yoshikawa et al. | 514/184 |
| 5,254,724 A | 10/1993 | Bergeron, Jr. | 560/312 |
| 5,292,771 A | 3/1994 | Backstrom et al. | 514/472 |
| 5,312,818 A | 5/1994 | Rubin et al. | 514/212 |
| 5,322,961 A | 6/1994 | Bergeron, Jr. | 562/623 |
| 5,324,738 A | 6/1994 | Dinan et al. | 514/325 |
| 5,331,013 A | 6/1994 | Ahlman et al. | 514/626 |
| 5,340,801 A | 8/1994 | Ewing et al. | 514/18 |
| 5,364,965 A | 11/1994 | Bergeron, Jr. | 562/623 |
| 5,367,113 A | 11/1994 | Bergeron, Jr. | 562/623 |
| 5,368,854 A | 11/1994 | Rennick | 424/85.2 |
| 5,391,555 A | 2/1995 | Marshall et al. | 514/311 |
| 5,493,053 A | 2/1996 | Bergeron, Jr. | 562/623 |
| 5,552,439 A | 9/1996 | Panetta | 514/534 |
| 5,569,680 A | 10/1996 | Wu | 514/786 |
| 5,599,795 A | 2/1997 | McCann et al. | 514/31 |
| 5,604,231 A | 2/1997 | Smith et al. | 514/256 |
| 5,691,343 A | 11/1997 | Sandborn | 514/262 |
| 5,693,645 A | 12/1997 | Sharpe et al. | 514/278 |
| 5,840,739 A | * 11/1998 | Bergeron, Jr. | 514/365 |
| 6,083,966 A | * 7/2000 | Bergeron, Jr. | 514/365 |
| 6,159,983 A | * 12/2000 | Bergeron, Jr. | 514/277 |
| 6,160,022 A | 12/2000 | Bergeron, Jr. | 514/674 |

FOREIGN PATENT DOCUMENTS

WO    WO94/11367    * 5/1994

OTHER PUBLICATIONS

Kato et al. Synthesis and Antihypertensive Activity of 5–(2–Hydroxyphenyl)–1–(3–mercaptopropionyl)–2–pyrrolidinecarboxylic Acids Chem. pharm. Bull. vol. 33, No. 11, pp. 4836–4846. 1985.*

Bergeron, et al. 'The Desferrithiocin Pharmacophore', J. Med. Chem. vol. 37, pp. 1411–1417.*
Singleton, *The Gastroenterology Annual*, pp. 268–310 (1983).
Kirsner et al., *N. Engl. J. Med.* vol. 306, pp. 775–837 (1982).
Hawthorne et al. *Brit. Med. J.*, vol. 305, p. 20 (1992).
Connell et al., *Gut.*, vol. 34 p. 1081 (1993).
Sharon et al., *Gastroenterology*, vol. 88, pp. 55–63 (1985) and vol. 86, pp. 453–460 (1984).
Kato et al., "Synthesis and Antihypertensive Activity 5–(2–hydroxyphenyl)–1–3–Mercaptopropionyl)–2–pyrrolidine-carboxylic Acids," *Chem. Pharm. Bull.*, 1985, vol. 33(11), pp. 4836–4846.
Bergeron et al., "The Desferrithiocin Pharmacophore," *J.Med. Chem.*, vol. 37, pp. 1411–1417 (1994).

* cited by examiner

*Primary Examiner*—Brenda Brumback
*Assistant Examiner*—Anish Gupta
(74) *Attorney, Agent, or Firm*—Miles & Stockbridge P.C.; Dennis P. Clarke

(57) ABSTRACT

A composition in unit dosage form for the inhibition, prevention or treatment of inflammatory bowel disease comprising an effective amount of a compound having the formula:

[A]

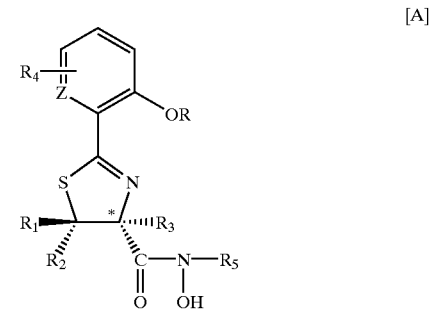

and a pharmaceutically acceptable carrier therefor. Also disclosed is a method for the inhibition, prevention or treatment of inflammatory bowel disease comprising administering to a human or non-human mammal in need thereof an effective amount of a compound having the formula:

[B]

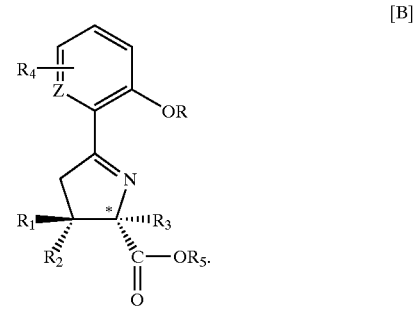

1 Claim, 8 Drawing Sheets

Control
7.5% Acetic Acid

**N- Methylhydroxamate
650 μ mol/kg**

JMXXVII – 168B
650 μ mol/kg

METHOD AND COMPOSITION FOR TREATMENT OF INFLAMMATORY BOWEL DISEASE

BACKGROUND OF THE INVENTION

Research leading to the completion of the invention was supported in part by Grant Nos. 3203522-12, RO1HL42817 and RO1DK49108 awarded by the National Institutes of Health (NIH). The United States Government has certain rights in and to the claimed invention.

1. Field of the Invention

The present invention relates to the treatment of inflammatory bowel diseases.

2. Description of the Prior Art

Inflammatory bowel disorders or diseases (IBD) encompass a spectrum of overlapping clinical diseases that appear to lack a common etiology. IBD, however, are characterized by chronic inflammation at various sites in the gastrointestinal (GI) tract. Illustrative IBD are regional enteritis (or Crohn's disease), idiopathic ulcerative colitis, idiopathic proctocolitis and infectious colitis. Most hypotheses regarding the pathogenesis of IBD concern the implication of immunologic, infectious and dietary factors.

IBD are characterized histopathologically by ulceration, pseudomembranes, radiologically visible lesions, edema and the build-up of inflammatory cells; symptoms involve diarrhea, abdominal pain, weight loss and hypoproteinemia. Descriptions in the literature include Northfield, *Drugs*, Vol. 14, pages 198–206 (1977); Blaker et al, *Eur. J. Pediatr.*, Vol. 139, pages 162–164 (1982); Singleton, *The Gastroenterology Annual*, pages 268–310 (1983); Saco et al, *J. Amer. Acad. Dermatol.*, Vol. 4, pages 619–629 (1981); Prantera et al, *Ital. J. Gastroenterol.*, Vol. 13, pages 24–27 (1981); Sales et al, *Arch. Int. Med.*, Vol. 143, pages 294–299 (1983); and Ament, *Inflammatory Bowel Diseases*, Martinus Nijhoff Publ., Boston, Mass., pages 254–268 (1982). Less frequent, but also possible, are mucosal inflammation of other sections of the GI tract, such as duodenitis, jejunitis and proctitis.

The clinical manifestations of ulcerative colitis and Crohn's disease share the common feature of inflammation. In ulcerative colitis, the earliest lesion is an inflammatory infiltration with abscess formation at the base of the crypts of Lieberkühn. Coalescence of these distended and ruptured crypts tends to separate the overlying mucosa from its blood supply, leading to ulceration. The inflammatory involvement is diffuse and superficial, usually limited to the mucosa and submucosa.

The clinical picture includes cramping, lower abdominal pain or rectal bleeding, soon followed by frequent, loose discharges consisting mainly of blood, pus and mucus with scanty fecal particles. The rectum and ampulla are usually found to be spastic.

In Crohn's disease (also known as regional enteritis or ulcerative ileitis), the most prominent feature of the disease is the granular, reddish-purple, edematous thickening of the bowel wall. In the early phase of the disease, the prominent irritability, spasm and edema give the appearance of a rigid contour to the diseased segment radiogenographically.

The histological picture consists of dilated and tortuous lymph vessels and granulomatous structures which are made up predominantly of epithelioid cells, lymphocytes and, occasionally, giant cells. With the development of inflammation, these granulomas often lose their circumscribed borders and merge with the surrounding tissue reaction. Obstruction is the predominant clinical feature. The stools, although loose, are rarely bloody.

Idiopathic ulcerative colitis (UC) is a recurrent acute and chronic ulcero-inflammatory disorder principally affecting the rectum and left colon, but sometimes the entire large bowel. See Kirsner et al, *N. Engl. J. Med.*, Vol. 306, pages 775–837 (1982). UC encompasses a spectrum of diffuse, continuous, superficial inflammation of the colon which begins in the rectum and extends to a variable proximal level. See *Cecil Textbook of Medicine*, 19th Edition, page 699, Wyngaarden et al, ed., (1992). Matters relating to the etiology (i.e., definitive etiopathogenesis is not known), epidemiology, pathogenesis, pathology, symptoms, diagnosis (e.g., endoscopy and radiography) and complications (e.g., cancer, intestinal complications such as rectal bleeding and toxic megacolon, and extraintestinal complications such as anemia and leukocytosis) are set forth in relatively complete detail in the *Cecil Textbook of Medicine*, supra.

The manner in which UC is treated can vary and, typically, the medical treatment depends upon the severity of the symptoms exhibited by the patient. Corticosteroids (e.g., prednisone), antibiotics (e.g., tetracycline, sulfatrimethoprim, metronidazole and cephalexin) and immunosuppressants (e.g., 6-mercaptopurine and azathioprine) often are used for treating UC. Anti-inflammatory agents (e.g., sulfasalazine and mesalamine) are effective to some degree in some patients for the treatment of acute UC. Certain anti-inflammatory agents are available commercially as Asacol from Rolm Pharma GmbH, Dipentum from Kabi Pharmacia AB and Rowasa [5-aminosalicylic acid (5-ASA)] from Solvay Pharmaceuticals. In more severe cases or when the anti-inflammatory agents fail to relieve the symptoms of UC, surgical procedures are used. Typical surgical procedures include colectomy, proctocolectomy and ileostomy. See *Cecil Textbook of Medicine*, supra. Other treatment methods for gastrointestinal disorders have been proposed in U.S. Pat. Nos. 5,110,795 (Hahn), 5,112,856 (Gaginella et al), 5,216,002 (Gidda et al), 5,238,931 (Yoshikawa et al), 5,292,771 (Backström et al), 5,312,818 (Rubin et al), 5,324,738 (Dinan et al), 5,331,013 (Ahlman et al), 5,340,801 (Ewing et al), 5,368,854 (Rennick), 5,391,555 (Marshall et al), 5,552,439 (Panetta), 5,569,680 (Wu), 5,599,795 (McCann et al), 5,604,231 (Smith et al), 5,691,343 (Sandborn) and 5,693,645 (Sharpe et al).

6-Mercaptopurine (6MP) and its prodrug azathioprine (AZA) have been used in the treatment of IBD for over twenty-five years. Multiple controlled trials and a recent meta-analysis support the efficacy of 6MP and AZA in Crohn's disease. See Willoughby et al, *Lancet*, Vol. ii, page 944 (1971); and Rosenberg et al, *Dig. Dis.*, Vol. 20, page 721 (1975). Several controlled trials support the use of AZA in ulcerative colitis, the most recent by Hawthorne et al in *Brit. Med. J.*, Vol. 305, page 20 (1992). However, use of 6MP and AZA has been limited by concerns about their toxicities. Dose-related leukopenia is seen in 2–5% of patients treated long-term with 6MP or AZA for IBD. See, for example, Present et al, *Am. Int. Med.*, Vol. 111, page 641 (1989); and Connell et al, *Gut*, Vol. 34, page 1081 (1993).

It is an object of the present invention to provide a novel and useful therapy for IBD.

SUMMARY OF THE INVENTION

Figure 1:
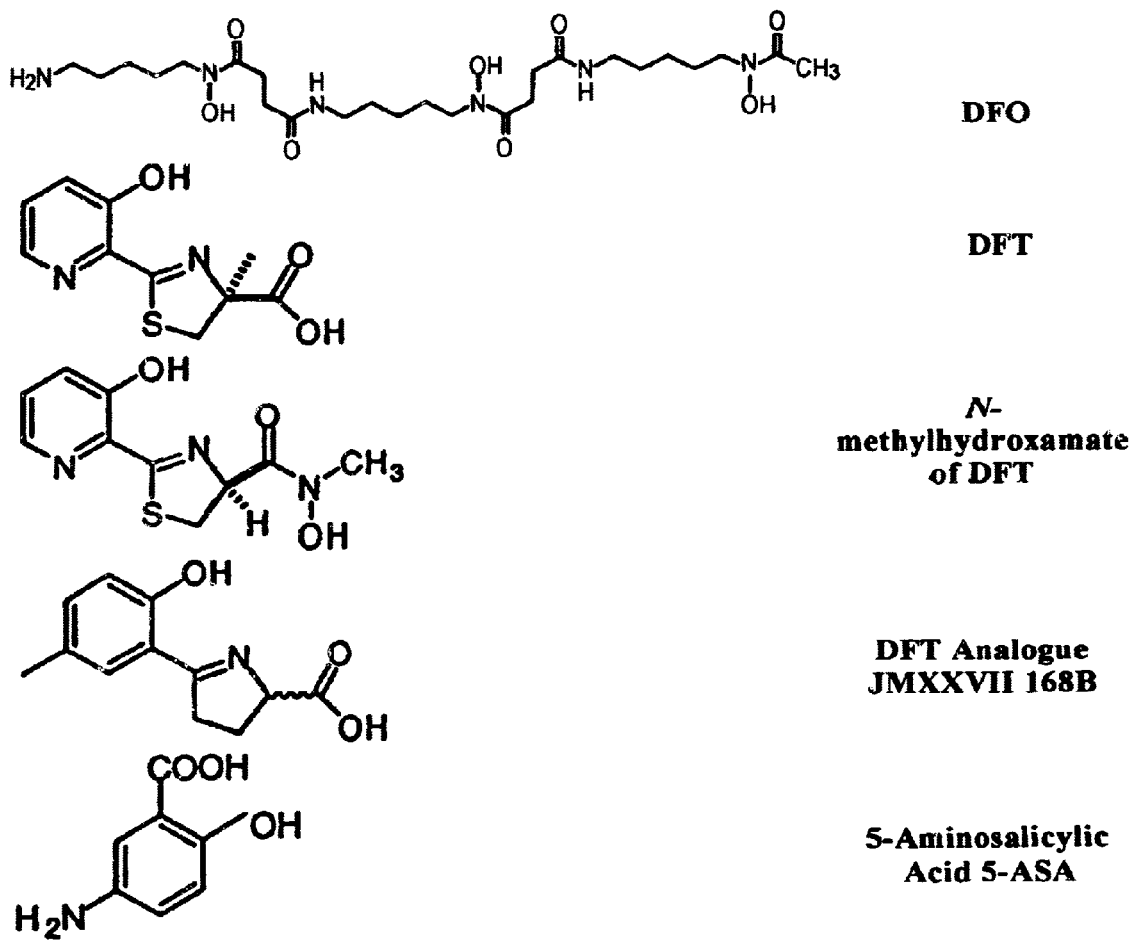
FIG. 1 sets forth the chemical formulae for various of the compounds described herein.
Figure 2:
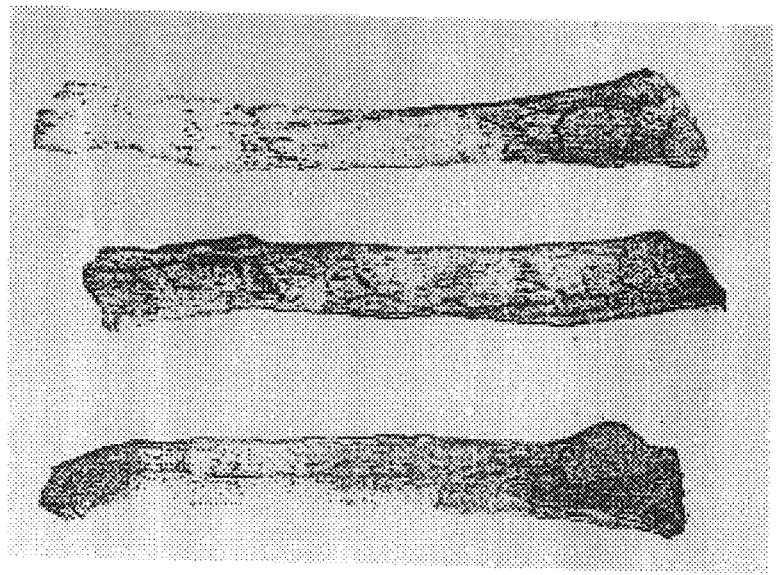
FIGS. 2–8 depict the results of tests performed on rat colons utilizing the methods and compositions of the present invention.
Figure 3:
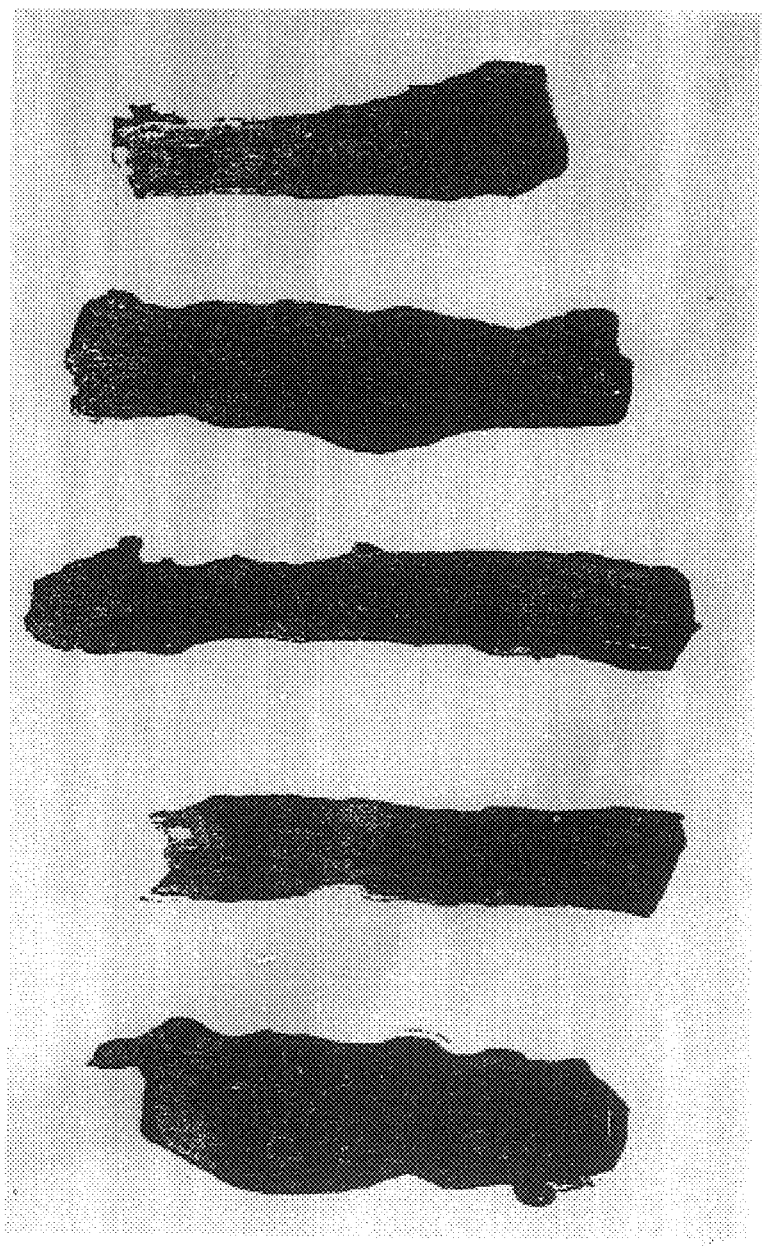
Figure 4:
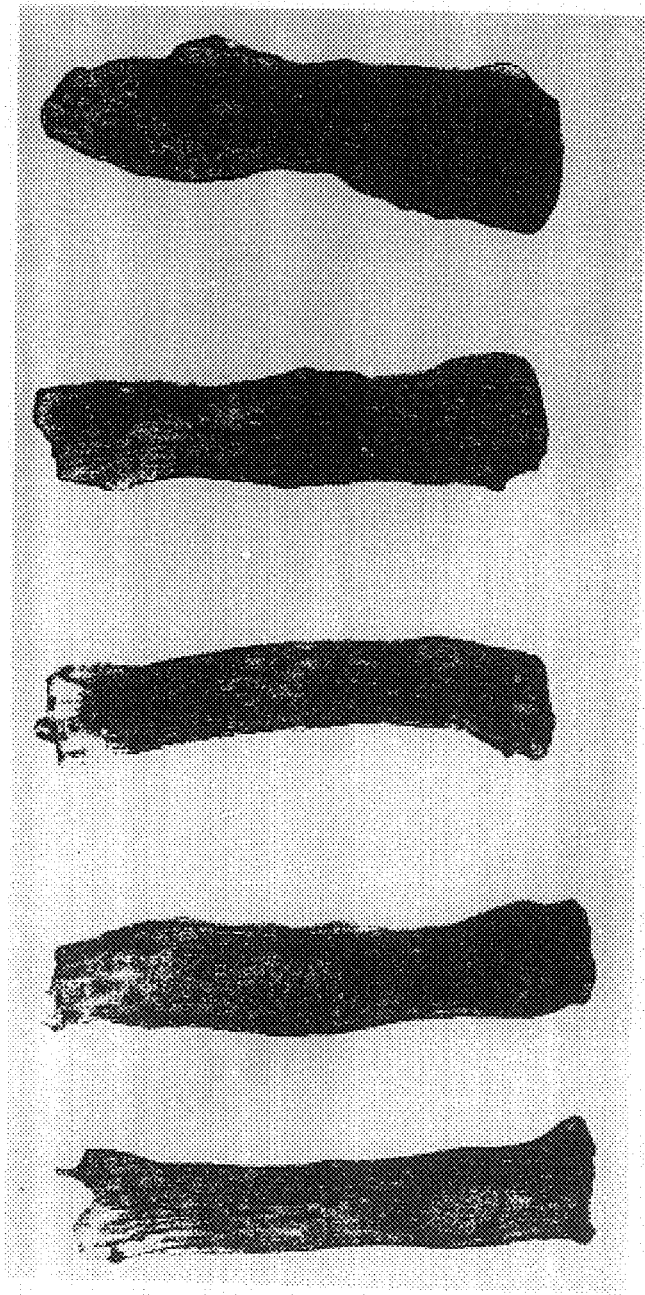
Figure 5:
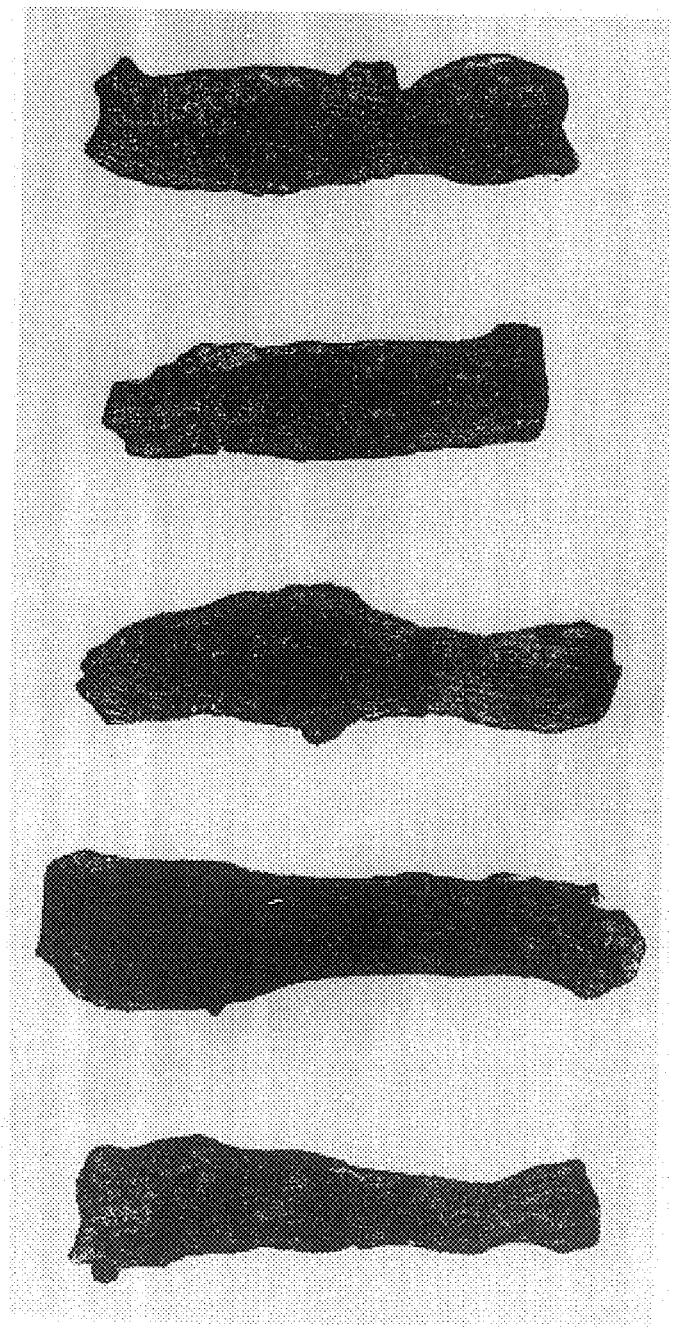
Figure 6:
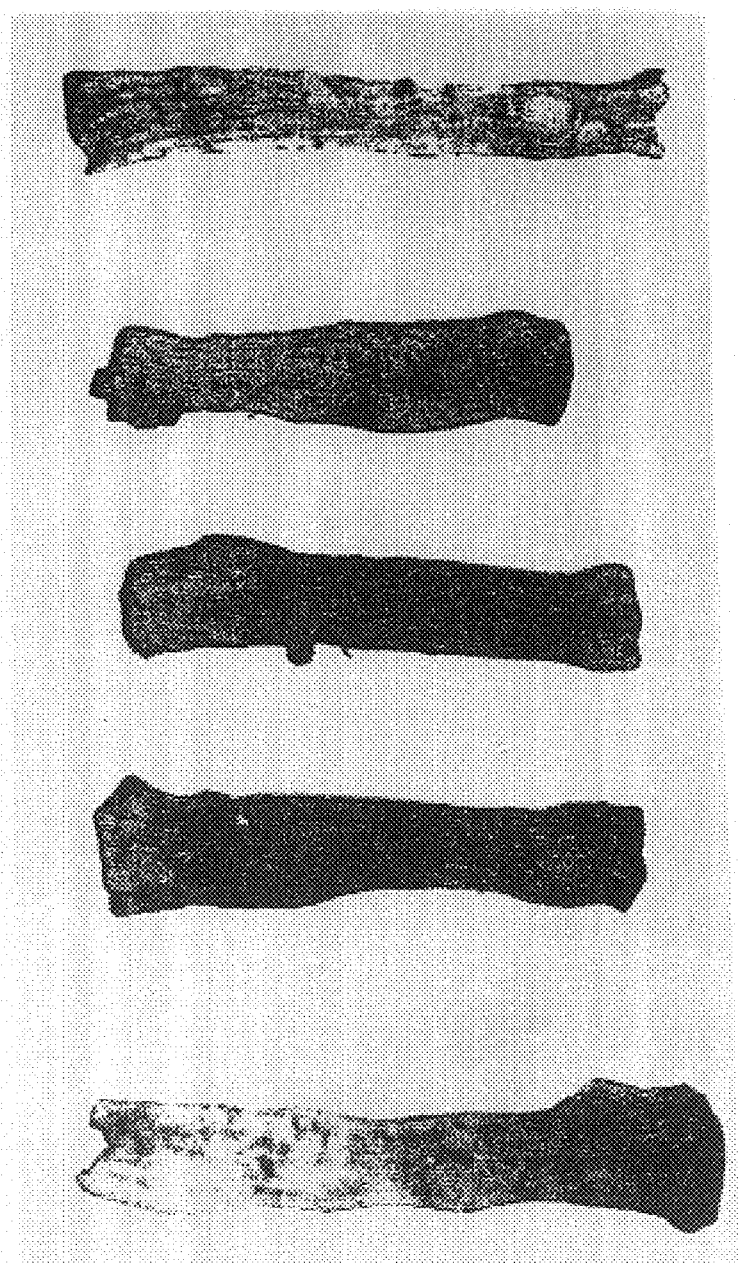

The above and other objects are realized by the present invention, one embodiment of which relates to a composition in unit dosage form for the inhibition, prevention or treatment of inflammatory bowel disease comprising an effective amount of a compound and a pharmaceutically acceptable carrier therefor, the compound having the formula:

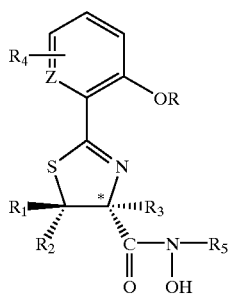

[A]

and the salts thereof with pharmaceutically acceptable acids and bases.

An additional embodiment of the invention concerns a novel method for the inhibition, prevention or treatment of inflammatory bowel disease comprising administering to a human or non-human mammal in need thereof an effective amount of a compound having the formula:

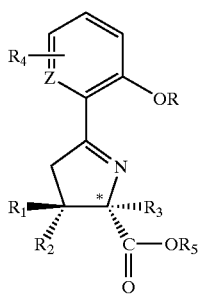

[B]

DETAILED DESCRIPTION OF THE INVENTION

The present invention is predicated on the discovery that IBD may be successfully prevented or treated and its onset greatly inhibited by treatment with one or more of the above-identified compounds. Moreover, some of these compounds have been shown to be virtually non-toxic, even at relatively massive dosages. Furthermore, the compounds of the invention have been found to be far superior to the conventionally employed 5-ASA for the treatment of IBD in animal models.

Several of the compounds employed in the compositions of the present invention, as well as methods for their preparation, are described in U.S. patent application Ser. Nos. 08/624,289 filed Mar. 29, 1996; and 09/144,103 filed Aug. 31, 1998, and U.S. Pat. Nos. 5,493,053; 5,322,961; 5,364,965; 5,367,113 and 5,254,724, the entire contents and disclosures of each of which are incorporated herein by reference.

The compounds of formula [B] may be prepared by esterifying p-cresol with 3-chloropropionyl chloride; heating the product with a Friedel-Crafts catalyst to give the β-chloroketone. Diethyl acetamidomalonate is C-alkylated with the chloroketone to yield an open-chain intermediate which is cyclized, e.g., by refluxing with concentrated HCl, to give the pyrrole carboxylic acid. The carboxylic acid group may then be esterified to give any desired ester.

More specifically, 3,4,-dihydro-5-(2-hydroxy-5-methylphenyl)-2H-pyrrole-2-carboxylic acid may be prepared as follows:

EXAMPLE

4-Methylphenyl 3-Chloropropanoate (19). 3-Chloropropionyl chloride (12.5 ml, 0.131 mol) was added for three minutes to a solution of p-cresol (12.90 g, 0.119 mol) in pyridine (9.5 ml, 0.12 mol) and $CH_2Cl_2$ (53 ml) at 0° C. After stirring the reaction mixture for one day at 0° C. to room temperature, solvent was removed by rotary evaporation. The concentrate was treated with brine (50 ml) and 0.5 M citric acid (150 ml) and extracted with EtOAc (3×100 ml). The organic extracts were washed with 100 ml; 1 N HCl, $H_2O$, cold 0.1 N NaOH, $H_2O$ and brine. After solvent removal, the residue was purified by silica gel flash column chromatography eluting with 7.5% EtOAc/hexane to give 12.90 g (55%) of 19 as a colorless liquid: NMR δ 2.34 (s, 3H), 3.03 (t, 2H, J=7), 3.86 (t, 2H, J=7), 6.95–7.01 (m, 2H), 7.17 (d, 2H, J=8).

2-(3-Chloropropionyl)-4-methylphenol (20). $AlCl_3$ (38.9 g, 0.292 mol) was added to 19 (12.89 g, 64.9 mmol); the exothermic reaction was controlled by brief cooling in ice water. The reaction mixture was heated at 90–95° C. with stirring under an $N_2$ balloon with periodic venting of the HCl for 69 minutes. The reaction flask was cooled to 0° C. and cold 0.5 N HCl (300 ml) was added, slowly at first. The aqueous phase was extracted with EtOAc (250 ml, 3×100 ml). The organic extracts were washed with $H_2O$ (100 ml) and brine (100 ml). After solvent removal, the solid was chromatographed on a silica gel flash column eluting with 26% $CH_2Cl_2$/pet ether yielding 10.21 g (79%) of 20 as a pale green solid: NMR δ 2.32 (s, 3H), 3.48 (t, 2H, J=7), 3.92 (t, 2H, J=7), 6.91 (d, 1H, J=8), 7.31 (dd, 1H, J=8, 2), 7.49 (s, 1H), 11.84 (s, 1H). Anal. calcd. for $C_{10}H_{11}ClO_2$: C 60.46, H 5.58. Found: C 60.72, H 5.63.

Diethyl acetamidomalonate (12.84 g, 59.11 mmol) was added to freshly prepared 0.29 M NaOEt (225 ml) in EtOH at 0° C. The solution resulting after brief sonication was transferred to an addition funnel and added over six minutes to a suspension of 20 (10.68 g, 53.74 mmol) in EtOH (50 ml) at 0° C. After stirring the reaction mixture for 18 hours at room temperature, solvent was removed in vacuo. Cold 0.25 N HCl (200 ml) was added and the aqueous phase was extracted with $CHCl_3$ (200 ml, 2×100 ml). The organic layer was washed with $H_2O$ (100 ml). After solvent removal, the solid was purified by silica gel flash column chromatography using 4% acetone/—$CH_2Cl_2$ to furnish 18.1 g (89%) of diethyl (acetylamino)[3-(2—hydroxy-5-methylphenyl)-3-oxopropyl]propanedioate (I) as a solid: NMR δ 1.26 (t, 6H, J=7), 2.04 (s, 3H), 2.30 (s, 3H), 2.78 (t, 2H, J=7), 2.98 (t, 2H, J=7), 4.17–4.34 (m, 4H), 6.79 (s, 1H), 6.88 (d, 1H, J=8), 7.25–7.30 (m, 1H), 7.47 (s, 1H), 11.97 (s, 1H). Anal. calcd. for $C_{19}H_{25}NO_7$: C 60.15, H 6.64, N 3.69. Found: C 60.23, H 6.73, N 3.77.

Concentrated HCl (140 ml) was added to I and the reaction mixture was heated at reflux under an $N_2$ balloon with periodic venting for 15 hours. Solvent was removed under high vacuum, the residue was dissolved in $H_2O$ (120 ml) and evaporation was repeated. Distilled $H_2O$(120 ml) was added to the solid and solvent was removed by lyophilization to give 12.96 g (quantitative) of 3,4-dihydro-5-(2-hydroxy-5-methylphenyl)-2H-pyrrole-2-carboxylic acid as a green solid: NMR ($D_2O$) δ 2.30 (s, 3H), 2.33–2.46 (m, 1H), 2.67–2.82 (m, 1H), 3.59–3.68 (m, 2H), 5.10 (dd, 1H, J=10, 6), 7.04 (d, 1H, J=8), 7.52–7.58 (m, 1H), 7.59–7.62 (m, 1H). Anal. calcd. for $C_{12}H_{14}ClNO_3$: C 56.37, H 5.52, N 5.48. Found: C 56.19, H 5.62, N 5.41.

Several of the compounds described above are characterized by the asymmetric carbon atom marked with an asterisk (*). The bonds surrounding these carbon atoms are arranged tetrahedrally and the substituents thus bonded to the asymmetric carbon atoms are in fixed positions. The formula represents optical antipodes exhibiting either the (S)- or (R)-conformation. Racemates can be split in a manner known per se, for example, after conversion of the optical antipodes into diastereoisomers, for example, by reaction with optically active acids or bases.

A typical model of IBD in acetic acid-induced colitis in the rat has been described by Krawisz et al in *Amer. J. Proc. Gastro. Col. Rec. Surg.*, Vol. 31, pages 11–18 (1980); and by Sharon et al in *Gastroenterology*, Vol. 88, pages 55–63 (1985) and Vol. 86, pages 453–460 (1984). Acetic acid-induced colitis is characterized by the movement of inflammatory cells into the colon, with the number of such cells in the mucosa being measured by the activity of myeloperoxidase, a marker enzyme for these cells. Positive desirable activity is indicated by a reduction in the high levels of myeloperoxidase caused by acetic acid.

Typically, Sprague-Dawley rats from Charles River Laboratories, Portage, Mich. (either sex, weight approximately 250 g) are dosed with test compounds and controls. Thereafter, the rats are given an intracolonic enema of acetic acid which produces a severe inflammatory response in the colon of a healthy rat characterized by rectal bleeding, diarrhea, epithelial erosions and destructions of crypts and gland cells. Twenty-four hours later, the test and control animals are sacrificed and the distal ten centimeters of the colons are removed and opened longitudinally. The tissue lesions contained within the removed, opened section of the colons are scored.

After the systematic evaluation of the impact of various fasting times, use of vehicles, the time interval between pre-treatment and administration of the acetic acid and altering the concentration of acetic acid, the final protocol for the experiments is to fast the rats for 30 hours in hanging wire cages, anesthetize the animals with sodium pentobarbital, administer the test drug 1 cc intrarectally (i.r.) either as a suspension or a solution in water, and to give the acetic acid (7.5% in water) 1 cc i.r. 30 minutes later. The rats are sacrificed 24 hours later and the colons are removed and assessed for damage.

The compounds tested against the above-described model are set forth in FIG. 1.

Results

Figure 7:
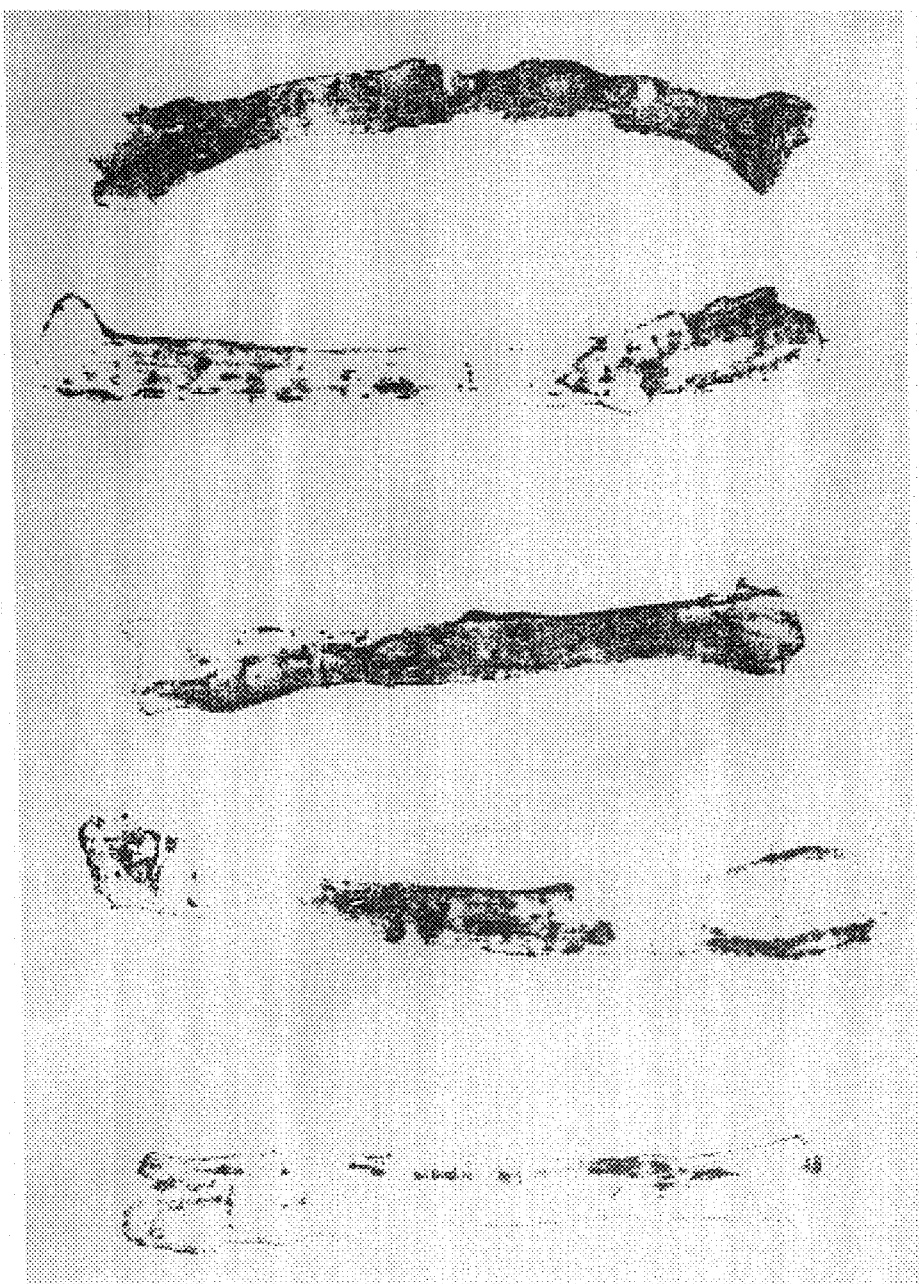
Figure 8:
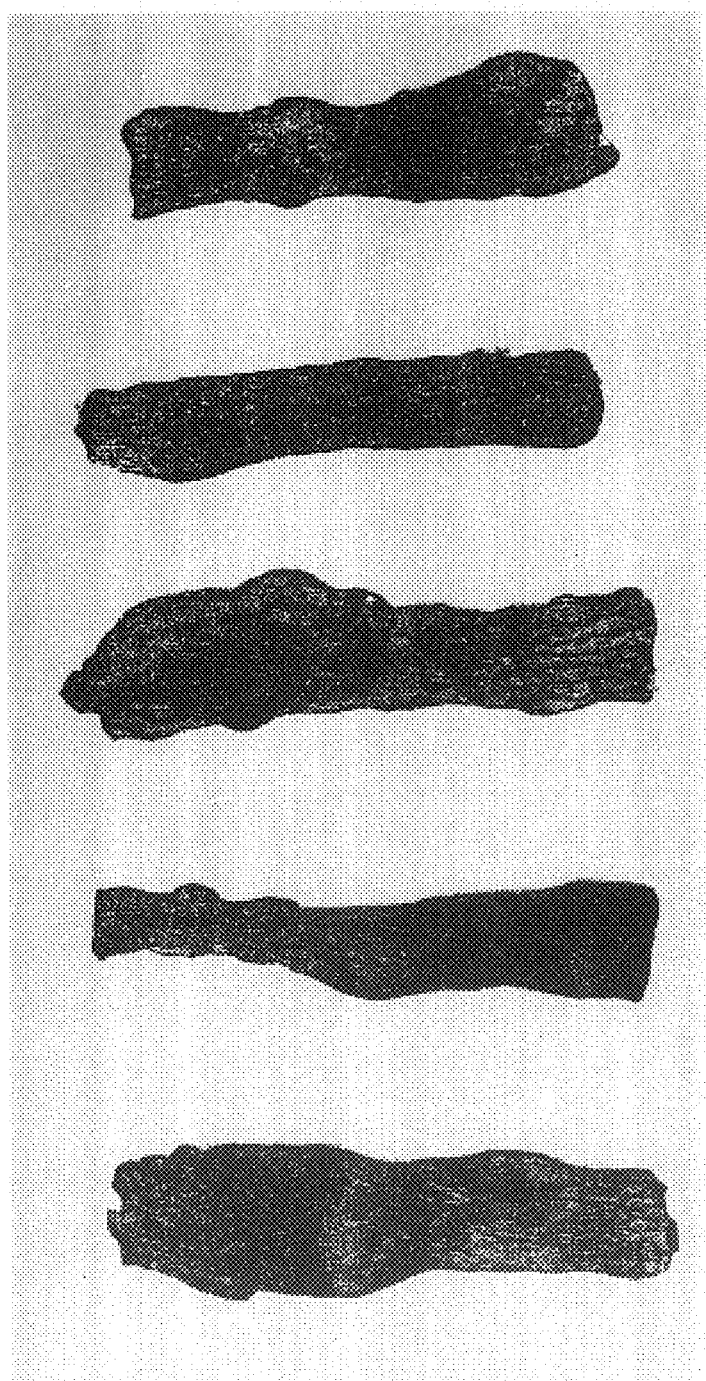

DFO and DFT given i.r. at a dose of 650 μmol/kg were ineffective. However, when either the N-methylhydroxamate or the 2H-pyrrolecarboxylic acid were given i.r. at 650 μmol/kg (165 or 166 mg/kg, respectively) 30 minutes before acetic acid, very little damage was noted in the colons of any of the test animals. See FIGS. 2–8. Experiments with the latter compound have been expanded, and very little damage has been noted in the colons of any of the rats treated with this compound. When the compound was evaluated head-to-head with 5-ASA or its commercially available formulation (Rowasa), the compound was found to be far superior even at a much lower dose (650 μmol/kg vs. 1742 μmol/kg). See, for example, FIGS. 7 and 8. In addition, preliminary acute toxicity studies in mice have shown the 2H-pyrrolecarboxylic acid to be virtually non-toxic, with no deaths even when injected intraperitoneally (i.p.) at doses up to 1 g/kg.

Thus, the results depicted in FIGS. 2–8 show that there is considerably less damage to the colons of rats treated with the 2H-pyrrolecarboxylic acid than to the colons of control rats. In further reversal studies, lesions in the group given the 2H-pyrrolecarboxylic acid 30 minutes after 2.5% acetic acid were less severe and less active than those in the control group. The lesions were apparently resolving and with some lamina proprial fibrosis and considerable hyperplasia of submucosal lymphoid tissue. A dose response study was performed with severe lesions being prevented in a majority of rats at a dose of 162.5 μmol/kg (41.5 mg/kg) at 1 cc i.r. This 2H-pyrrolecarboxylic acid is a relatively easy and inexpensive molecule to synthesize. In addition, although the drug binds iron remarkably well in a test tube, it has been found to be inactive as an iron chelator when given to rats orally or subcutaneously (s.c.). This is a highly desirable property, as patients suffering from IBD are already anemic due to disease-related blood loss.

It has been established, therefore, that the compounds used in the method of the present invention can treat inflammatory bowel disease. The term "inflammatory bowel disease," as used for purposes of the present invention, means any disorder of the digestive system which is characterized by inflammation. Examples of such disorders include Crohn's disease, mucous colitis, ulcerative colitis, pseudomembranous enterocolitis, non-specific colonic ulcers, collagenous colitis, cathartic colon, ulcerative proctitis, radiation enteritis and colitis, idiopathic diffuse ulcerative non-granuloma-tous enteritis, non-steroidal anti-inflammatory drug induced inflammations, celiac sprue and the like.

The method of the present invention comprises administering to a mammal suffering from inflammatory bowel disease an effective amount of one or more of the compounds of the invention. Administration may be accomplished either therapeutically or prophylactically by means of pharmaceutical compositions which are prepared by techniques well known in the pharmaceutical sciences.

While the compounds of the invention are preferably administered orally or intrarectally, they may also be administered by a variety of other routes such as transdermally, subcutaneously, intranasally, intramuscularly and intravenously.

The present invention is also directed to pharmaceutical compositions which include at least one compound as described above in association with one or more pharmaceutically acceptable diluents, excipients or carriers therefor.

In making the pharmaceutical compositions of the present invention, one or more compounds will usually be mixed with, diluted by or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 60% by weight of active compound, soft and hard gelatin capsules, suppositories, sterile injectable solutions and sterile packaged powders.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide rapid, sustained or delayed release of the active ingredient after administration to the patient by employing procedures well known in the art.

The dose of the compound is that amount effective to prevent occurrence of the symptoms of the disease or to treat some symptoms of the disease from which the patient suffers. By "effective amount," "therapeutic amount" or "effective dose" is meant that amount sufficient to elicit the desired pharmacological or therapeutic effects, thus resulting in effective prevention or treatment of the disease. Prevention of the disease is manifested by a prolonging or delaying of the onset of the symptoms of the disease. Treatment of the disease is manifested by a decrease in the symptoms associated with the disease or an amelioration of the recurrence of the symptoms of the disease.

The effective dose may vary, depending upon factors such as the condition of the patient, the severity of the symptoms of the disease and the manner in which the pharmaceutical composition is administered.

The compositions are formulated, preferably in a unit dosage form, such that each dosage contains from about 100 to about 12,000 mg, more usually about 250 to about 6,000 mg, of the active ingredient. The term "unit dosage form" refers to physically discrete units suitable as unitary dosages for human subjects and other mammals, each unit containing a predetermined quantity of active material calculated to produce the desired therapeutic effect, in association with one or more of the above-described suitable pharmaceutical diluents, excipients or carriers.

The compounds are effective over a wide dosage range in treating IBD. Thus, as used herein, the term "effective amount" refers to a dosage range of from about 1 to about 3,000 mg/kg of body weight per day. In the treatment of adult humans, the range of about 2 to about 500 mg/kg, in single or divided doses, is preferred. However, it will be understood that the amount of compound actually administered will be determined by a physician in light of the relevant circumstances, including (1) the condition to be treated, (2) the choice of compound to be administered, (3) the chosen route of administration, (4) the age, weight and response of the individual patient, and (5) the severity of the patient's symptoms. Therefore, the above dosage ranges are not intended to limit the scope of the invention in any way.

I claim:

1. A method for the inhibition, or treatment of inflammatory bowel disease comprising administering to a human or non-human mammal in need thereof an effective amount of a compound having the formula:

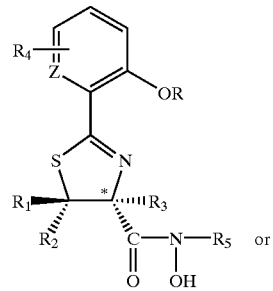

[A]

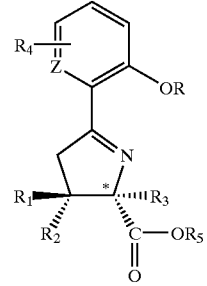

[B]

wherein: Z is CH or N;

R is H or acyl;

$R_1$, $R_2$, $R_3$ and $R_5$ may be the same or different and represent H, alkyl or hydrocarbyl arylalkyl having up to 14 carbon atoms; and $R_4$ is H, alkyl having 1–6 carbon atoms or OR.

* * * * *